US012180791B2

(12) United States Patent
Olivares Antunez et al.

(10) Patent No.: US 12,180,791 B2
(45) Date of Patent: Dec. 31, 2024

(54) METHOD AND SYSTEM FOR DRILLING FLUID MONITORING

(71) Applicant: SAUDI ARABIAN OIL COMPANY, Dhahran (SA)

(72) Inventors: Tulio D. Olivares Antunez, Khobar (SA); Walid Zahrani, Dammam (SA); Rafael M. Pino, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 18/056,608

(22) Filed: Nov. 17, 2022

(65) Prior Publication Data

US 2024/0167347 A1    May 23, 2024

(51) Int. Cl.
| | | |
|---|---|---|
| *E21B 21/01* | (2006.01) | |
| *E21B 21/06* | (2006.01) | |
| *E21B 21/08* | (2006.01) | |
| *G01N 33/28* | (2006.01) | |

(52) U.S. Cl.
CPC ............ *E21B 21/01* (2013.01); *E21B 21/062* (2013.01); *E21B 21/08* (2013.01); *G01N 33/2823* (2013.01)

(58) Field of Classification Search
CPC ........ E21B 21/08; E21B 21/01; E21B 21/062; G01N 33/2823
See application file for complete search history.

(56) References Cited

U.S. PATENT DOCUMENTS

| | | | |
|---|---|---|---|
| 4,369,655 A | * | 1/1983 | Scearce .................. G01N 15/06 73/152.49 |
| 9,587,489 B2 | | 3/2017 | Van Zuilekom et al. |
| 10,760,416 B2 | | 9/2020 | Weng et al. |
| 2018/0003045 A1 | * | 1/2018 | Dotson .................... G01F 1/663 |
| 2018/0058992 A1 | * | 3/2018 | van Oort ................ G01N 11/02 |
| 2018/0135367 A1 | * | 5/2018 | Thow .................... E21B 21/067 |
| 2019/0055797 A1 | | 2/2019 | Astrid et al. |
| 2021/0130674 A1 | * | 5/2021 | Amanullah .............. C09K 8/04 |
| 2021/0148215 A1 | * | 5/2021 | Jamison .................. E21B 44/04 |
| 2022/0243543 A1 | * | 8/2022 | Abughaban ............. B01F 23/51 |
| 2022/0275695 A1 | | 9/2022 | Haughs |

FOREIGN PATENT DOCUMENTS

| | | |
|---|---|---|
| WO | 2020139352 A1 | 7/2020 |
| WO | 2020263252 A1 | 12/2020 |
| WO | 2022087037 A1 | 4/2022 |

OTHER PUBLICATIONS

International Search Report and Written Opinion issued in corresponding International Application No. PCT/US2023/079789, dated Jan. 24, 2024 (11 pages).

* cited by examiner

*Primary Examiner* — Brad Harcourt
(74) *Attorney, Agent, or Firm* — Osha Bergman Watanabe & Burton LLP (57) ABSTRACT

A method includes mixing, in an active pit, a drilling fluid to be introduced to a wellbore; receiving, through a flowline, the drilling fluid from the wellbore; obtaining sensor data, using one or more sensor coupled to at least one of the active pit and the flowline, on at least one of coefficient of friction and lubricant content of the drilling fluid; and determining, using an automated control system, whether a lubricant needs to be added to the drilling fluid based on the sensor data.

12 Claims, 4 Drawing Sheets

METHOD AND SYSTEM FOR DRILLING FLUID MONITORING

BACKGROUND

In oilfield engineering, drilling fluids are used to aid the drilling of wellbores into the ground. In particular, the drilling fluids serve various functions to maintain wellbore stability, such as controlling formation pressures, removing drill cuttings out of the wellbore, providing hydrostatic pressure to prevent formation fluids from entering the wellbore, keeping the drill bit cool and clean during drilling, lubricating, and suspending the drill cuttings while drilling is paused or when the drilling assembly is brought in and out of the wellbore.

The drilling fluid, depending on its continuous phase, may include: water-based mud (WBM), which can be dispersed and non-dispersed; non-aqueous mud, usually an oil-based mud (OBM); and gaseous drilling fluid, in which a wide range of gases can be used. Along with their formatives, the drilling fluids may also include one or more additives for drilling various oil and gas formations.

Drilling fluid compositions may vary based on wellbore demands, rig capabilities and environmental concerns, and may be designed to control subsurface pressures, minimize formation damage, minimize the potential for lost circulation, control erosion of the borehole, and optimize drilling parameters such as penetration rate and hole cleaning.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method that includes mixing, in an active pit, a drilling fluid to be introduced to a wellbore; receiving, through a flowline, the drilling fluid from the wellbore; obtaining sensor data, using one or more sensor coupled to at least one of the active pit and the flowline, on at least one of coefficient of friction and lubricant content of the drilling fluid; and determining, using an automated control system, whether a lubricant needs to be added to the drilling fluid based on the sensor data. The determination may be made by comparing the sensor data with a predetermined value. The method may further include obtaining, by a user device, the predetermined value. The method may also include selecting a type of lubricant based on whether the drilling fluid contains water-based mud or oil-based mud. The method may also include calculating an additional amount of lubricant needed to comply with the predetermined value. The calculating is based on a volume of the drilling fluid in circulation and a difference between the sensor data and the predetermined value. A command may then be transmitted, from the automated control system, to cause the additional amount of lubricant to be supplied to the drilling fluid.

In general, in one aspect, embodiments relate to a system that includes an active pit containing a drilling fluid to be introduced to a wellbore; a flowline receiving the drilling fluid from the wellbore; one or more sensor coupled to at least one of the active pit and the flowline and configured to obtain sensor data on at least one of coefficient of friction and lubricant content of the drilling fluid; and an automated control system configured to make a determination on whether a lubricant needs to be added to the drilling fluid based on the sensor data. The automated control system is configured to make the determination by comparing the sensor data with a predetermined value. The system further comprises a user device for inputting the predetermined value. The automated control system is configured to select a type of lubricant based on whether the drilling fluid contains water-based mud or oil-based mud. The automated control system is also configured to calculate an additional amount of lubricant needed to comply with the predetermined value, which may be based on a volume of the drilling fluid in circulation and a difference between the sensor data and the predetermined value. The automated control system may then transmit a command to cause the additional amount of lubricant to be supplied to the drilling fluid.

Other aspects and advantages of the claimed subject matter will be apparent from the following description and the appended claims.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

In general, embodiments of the disclosure include systems and methods for drilling fluid processing using real-time sensors and control systems. In particular, real-time compositional and characteristics data of a drilling fluid may be collected from sensors disposed at one or more stages of the drilling process. The collected data may be analyzed and may be used to instruct mixing of the drilling fluid to achieve desired drilling fluid characteristics and performance, which may be used for torque reduction for a smooth and safe drilling process, thus increasing drilling fluid quality and drilling efficiency.

Figure 1:
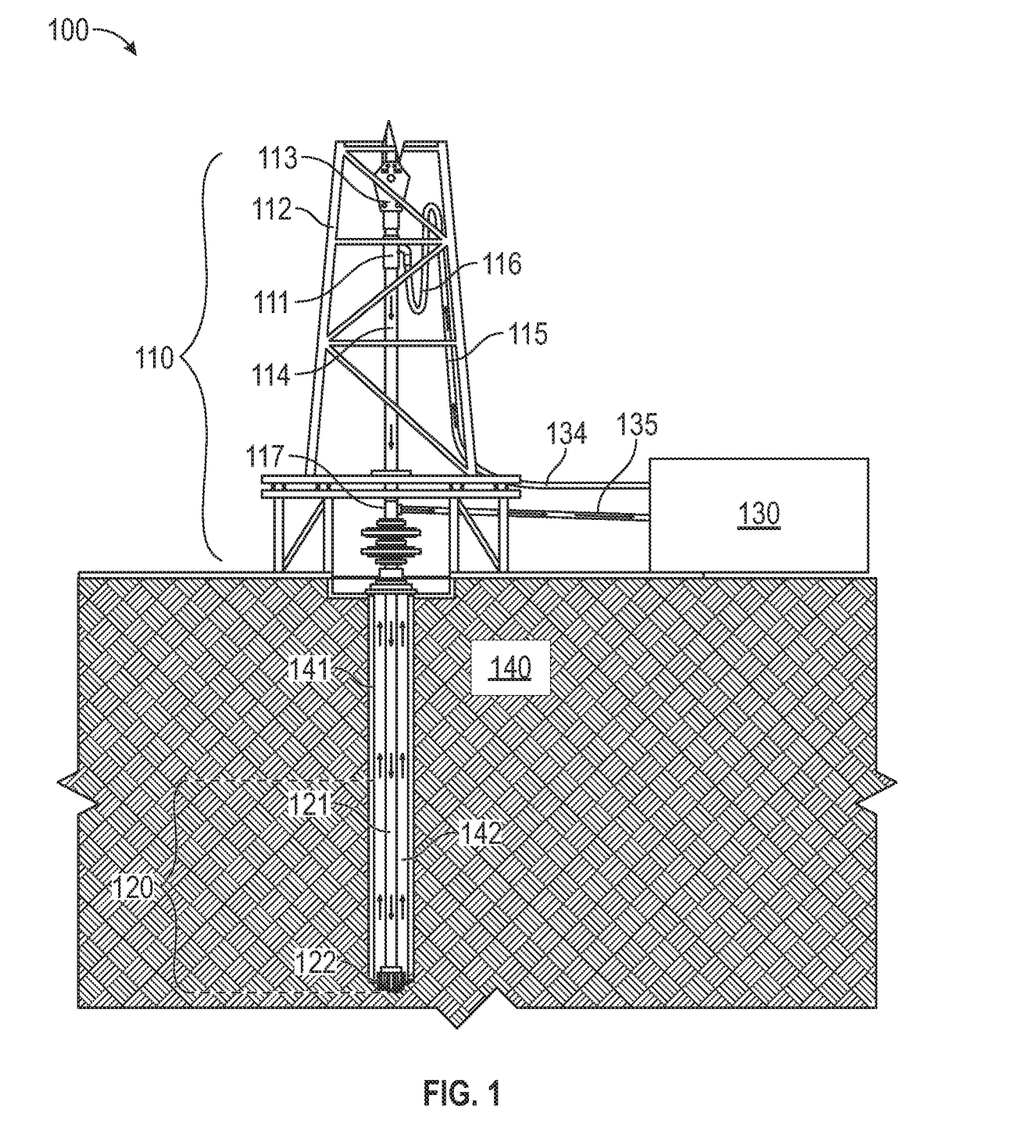
FIG. 1 shows a schematic diagram of a drilling system in accordance with one or more embodiments.

FIG. 1 shows a schematic diagram of a drilling system in accordance with one or more embodiments. As shown in FIG. 1, a drilling system 100 may include a drilling rig 110 arranged around a drill bit logging tool 120 in a wellbore 140, and a drilling fluid processing system 130.

The drilling rig 110 may have various configurations. In the non-limiting example shown in FIG. 1, a top drive 111 is suspended in a derrick 112 by a travelling block 113. The top drive 111 may rotate a drive shaft (not shown), such that the drill bit logging tool 120 may cut the rock at a bottom of the wellbore 140. A kelly 114 is coupled to the top drive and extends downhole to the wellbore 140.

A casing 141 may be inserted into the wellbore 140. The sides of the wellbore may require support, and thus the casing may be used for supporting the sides of the wellbore.

The space between the casing 141 and the untreated sides of the wellbore 140 may be cemented to hold the casing in place. The cement may be forced through a lower end of the casing and into an annulus 142 between the casing 141 and a wall of the wellbore 140. The drill bit logging tool 120 may be disposed in the casing 141, including at least a drill string 121 and a drill bit 122 disposed at a bottom of the wellbore 140. The drill bit 122 is arranged at the end of the drill string 121, cutting the rock at the bottom of the wellbore 140.

During drilling, a drilling fluid is introduced downhole and is constantly circulated in the drilling system. Specifically, the drilling fluid may be extracted from a discharge line 134 of the drilling fluid processing system 130, and is introduced downhole through a standpipe 115, a rotary hose 116, the top drive 111, and the kelly 114. The drilling fluid is then sent through the drill string 121 and out of the drill bit 122 to aid in the drilling of the wellbore 140. After passing through the drill bit 122, the used drilling fluid travels back to the drilling fluid processing system 130 on the surface. Specifically, the used drilling fluid travels up the annulus 142 between the drill string 121 and the wellbore 140, picking up the drill cuttings up the hole. Once the used drilling fluid reaches a bell nipple 117 on the drilling rig 110 at the surface, the used drilling fluid goes through a flowline 135 back to the drilling fluid processing system 130.

While only a number of structures are disclosed in FIG. 1, a person having ordinary skill in the art would appreciate that the drilling system may include other structures as needed. The drilling fluid processing system 130 of the present disclosure may also apply to other drilling systems, for example, a drilling system having other types of drilling rigs or platform drilling systems.

Figure 2:
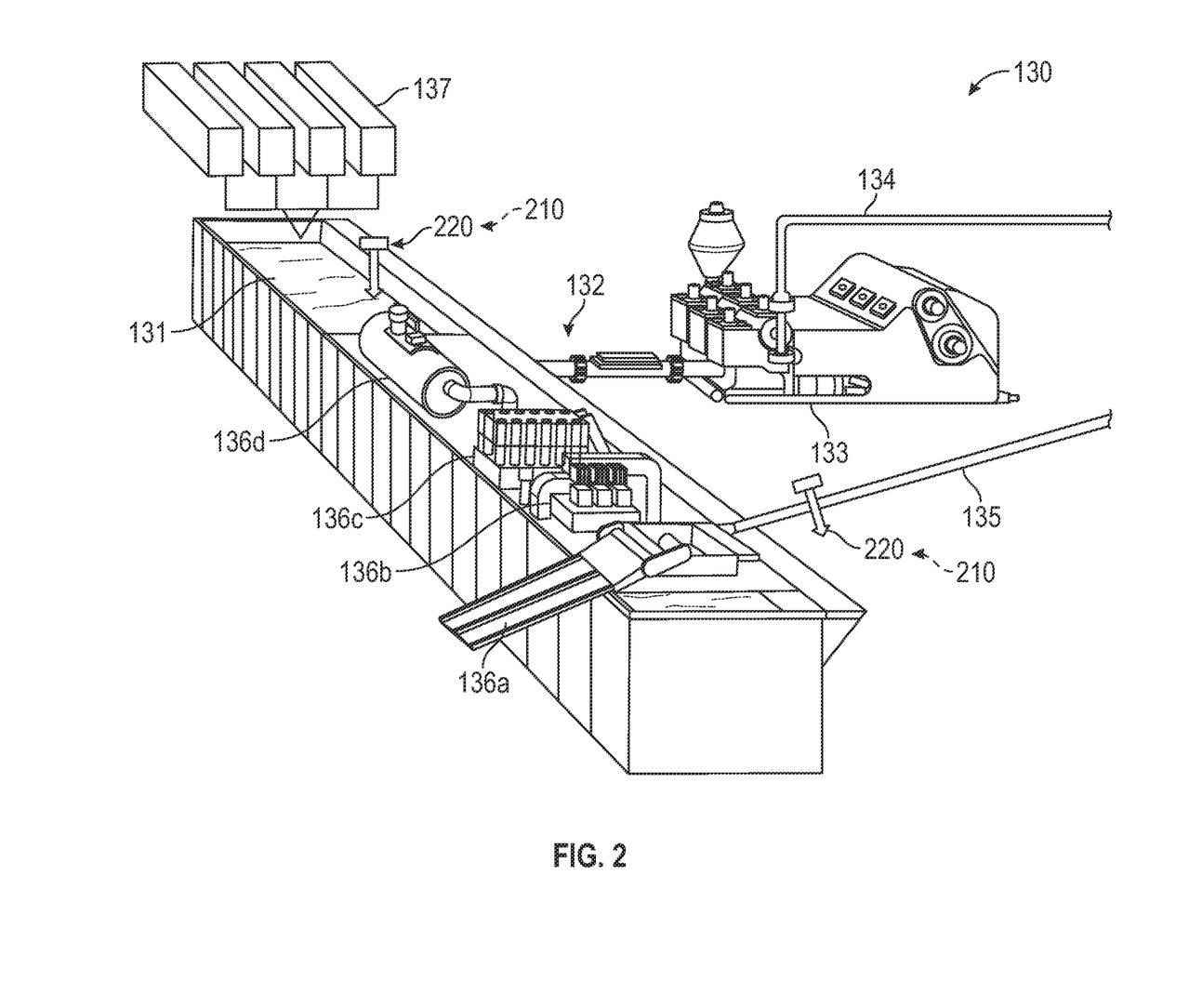
FIG. 2 shows a schematic diagram of a drilling fluid processing system in accordance with one or more embodiments.

FIG. 2 show a schematic diagram of a drilling system in accordance with one or more embodiments. Specifically, FIG. 2 shows a non-limiting example of the drilling fluid processing system 130 and other relevant structures involved in circulation of the drilling fluid during a drilling process. The drilling fluid processing system 130 may include, an active pit 131, which may be a container or other type of receptacle for mixing one or more components, such as various liquids, fresh mud, recycled mud, additives, and/or other chemicals, to produce a drilling fluid. In one or more embodiments, the drilling fluid processing system 130 may comprise one or more supply tank 137 supplying the one or more components to the active pit 131. The supply tank(s) 137 may be mud supply tanks, additive supply tanks, dry/wet feeders, and may be equipped with or coupled to one or more control valves for managing the mixing of components. Control valves may be used to manage inputs into the active pit, and may be coupled with volume or weight sensors, flow meters, etc.

The drilling fluid processing system 130 may include various types of drilling fluid equipment, such as various pumps, mud lines, liquid supply lines, and/or other mixing equipment. In the non-limiting example shown in FIG. 2, the drilling fluid processing system 130 may comprise a suction line 132, a mud pump 133, a discharge line 134, and a return flowline 135 returning used drilling fluid. In one or more embodiments, the drilling fluid processing system may also include one or more filter equipment for removing particular solids, for example, a shale shaker 136a, a desander 136b, a desilter 136c, and a degasser 136d. Filter equipment may be used to filter, for example, drill cuttings and coarse aggregates from used drilling fluid in order to recycle drilling fluid.

During circulation, a drilling fluid is mixed in the active pit 131, subsequently pumped through the suction line 132 and the discharge line 134, using the mud pump 133, to the drilling rig 110. After circulation, a used drilling fluid travels up the annulus between the drill string and the wellbore, picking up and carrying the drill cuttings up the hole, where the used drilling fluid is directed back to the drilling fluid processing system 130 through the return flowline 135. The used drilling fluid may be processed through one or more of the shale shaker 136a, the desander 136b, the desilter 136c, and the degasser 136d for recycling, and the recycled drilling fluid may be introduced to the active pit 131 for recirculation.

To provide a drilling fluid with specific properties and to control the parameters in the drilling operations, the drilling system according to one or more embodiments may further comprise an automated control system 210 and one or more sensor 220.

Drilling fluid properties may correspond to different physical qualities associated with the drilling fluid, such as specific gravity values, viscosity levels, pH levels, rheological values such as flow rates, temperature values, resistivity values, mud mixture weights, mud particle sizes, and various other attributes that affect the role of drilling fluid in a wellbore. The drilling parameters associate with parameters applied during circulation of the drilling fluid, such as flow rate, pump pressure, torque, revolution per minute, and weight on bit.

The drilling fluid may include water-based mud (WBM) or oil-based mud (OBM). The WBM is a mud in which water is the major continuous phase as well as the wetting phase. The WBM may include water in an amount of at least 50 volume percent of the entire composition. The WBM may include fresh water, or saltwater containing varying amount of dissolved sodium or calcium chloride as a major component. Oil may also present, in a small amount not exceeding the amount of water, such that the drilling fluid will retain its character as a water continuous phase material.

The OBM is a mud in which oil is the major continuous phase. The OBM may comprise one or more oil, such as diesel, kerosene, fuel oil, selected crude oil, or mineral oil. The OBM may include the oil in an amount of at least 50 volume percent of the entire composition. Water may also present, in a small amount not exceeding the amount of oil, as a dispersed phase in conjunction with one or more additives.

The drilling fluid may comprise additives to achieve various effects, such as viscosifiers, weighting agents for density control, fluid loss control agents, lubricants, emulsifiers, corrosion inhibitors, salts, and buffering agents. The amount of additives in the drilling fluid may be different for WBM and OBM and may be determined according to the drilling fluid continuous phase.

A viscosifier is an additive with functionality for providing thermal stability, hole-cleaning, shear-thinning, improving carrying capacity as well as modifying other attributes of the mud. Examples of viscosifiers include bentonite, inorganic viscosifiers, polymeric viscosifiers, low-temperature viscosifiers, high-temperature viscosifiers, oil-fluid liquid viscosifiers, organophilic clay viscosifiers, and biopolymer viscosifiers. A weighting agent is a material that, when added to drilling fluid, increases its density. Examples of weighting agents may include barite, hematite, calcium carbonate, siderite, etc. A buffering agent may be a pH buffering agent that causes a mud to resist changes in pH levels. For example, a buffering agent may include water, a weak acid (or weak base) and salt of the weak acid (or a salt of weak base). An emulsifier may be a chemical used in producing an oil-based or synthetic oil-based drilling fluid that forms a water-in-oil emulsion. In particular, an emulsifier may lower the interfacial tension between oil and water. For example, emulsifiers may be a primary emulsifier or a secondary emulsifier, where the secondary emulsifier is rarely used alone in producing a drilling fluid. Emulsifiers may include calcium fatty-acid soaps made from various fatty acids and lime, and/or derivatives such as amides, amines, amidoamines and imidazolines made by reactions of fatty acids, and various ethanolamine compounds. A lubricant may be a material that reduces coefficient of friction, torque, and drag between the drill strings and rock formation in wellbores, so as to reduce stuck pipe risk and increase rate of penetration (ROP) and bit life. Examples of lubricants for WBM may include blends of fatty amides acid and esters, polyol ester of fatty acids, diamine and fatty acid with alcohol amide in vegetable oil, or blends of surfactants. The lubricants for WBM may be used in a range of from 1 to 3 percent volume by volume (% V/V). Examples of lubricants for OBM may be a liquid blend of polymeric fatty acid ester in a concentration of from 2 to 5% V/V.

The type and amount of additives in a drilling fluid may be selected, at least in part, based on the well in which the drilling fluid is being used. For example, in vertical wells (with no or little inclination), there may be less torque and friction issues from drilling operations when compared with horizontal wells (with higher inclination). Thus, a drilling fluid with a relatively smaller amount of lubricant may be used in vertical wells when compared with horizontal wells.

A specific drilling fluid property and drilling parameters may be selected by the automated control system to have desired predetermined values, where a predetermined value may present as a range of acceptable values, a specific threshold value that should be exceeded, a precise scalar quantity, etc. In one or more embodiments, the automated control system may obtain real-time data from one or more sensor measuring various drilling fluid properties and drilling parameters. Examples of sensors include pH sensors, viscosity sensors, density sensors, rheological sensors, volume sensors, weight sensors, pressure sensors, flow meters, revolution per minute sensor, coefficient of friction sensor, etc. Likewise, sensor data may refer to both raw sensor measurements and/or processed sensor data associated with one or more drilling fluid properties and drilling parameters. The sensor may be equipped with signal transmitting and/or receiving capability to communicate sensor data with the automated control system.

A sensor according to one or more embodiments may be used to measure a content of a specific component in the drilling fluid. In one or more embodiments, the sensor may be a lubricant content sensor that measures the lubricant content in volume. In one or more embodiments, the lubricant content sensor may be an oil water ratio sensor.

A sensor according to one or more embodiments may be used to measure a coefficient of friction of the drilling fluid. Due to the complexity of wellbore geometry in drilling operations and high torque and drag forces, it is important to minimize the coefficient of friction to avoid excessive torque and axial drag that cause mechanical erosion on the drill string. The coefficient of friction sensor may be an electrical sensor, a tribosensor, or any other types of sensor known to one having ordinary skill in the art that can measure the friction coefficient between materials.

According to one or more embodiments, the one or more sensor may be disposed at one or more positions in the drilling system, along a flow path of the drilling fluid. In one or more embodiments, the sensor may be disposed in the active pit of the drilling system to obtain real-time sensor data on the drilling fluid before being introduced to the wellbore. In one or more embodiments, the sensor may be disposed in the return flowline to obtain real-time sensor data on the used drilling fluid. Alternatively, the sensor may be disposed in any structure or connecting lines of the drilling system disclosed in FIGS. 1 and 2 and accompanying description. The sensor data obtained from one or more positions may be sent to a computer in the automated control system for processing, or may be sent after processed in the sensor. The sensor data obtained from one or more positions may be compared with each other, or may be compared to the predetermined value, so as to instruct a computer in the automated control system to adjust amount of additives (e.g., lubricant) for desired drilling fluid property and/or to adjust drilling parameters for smooth and safe drilling operations.

Figure 3:
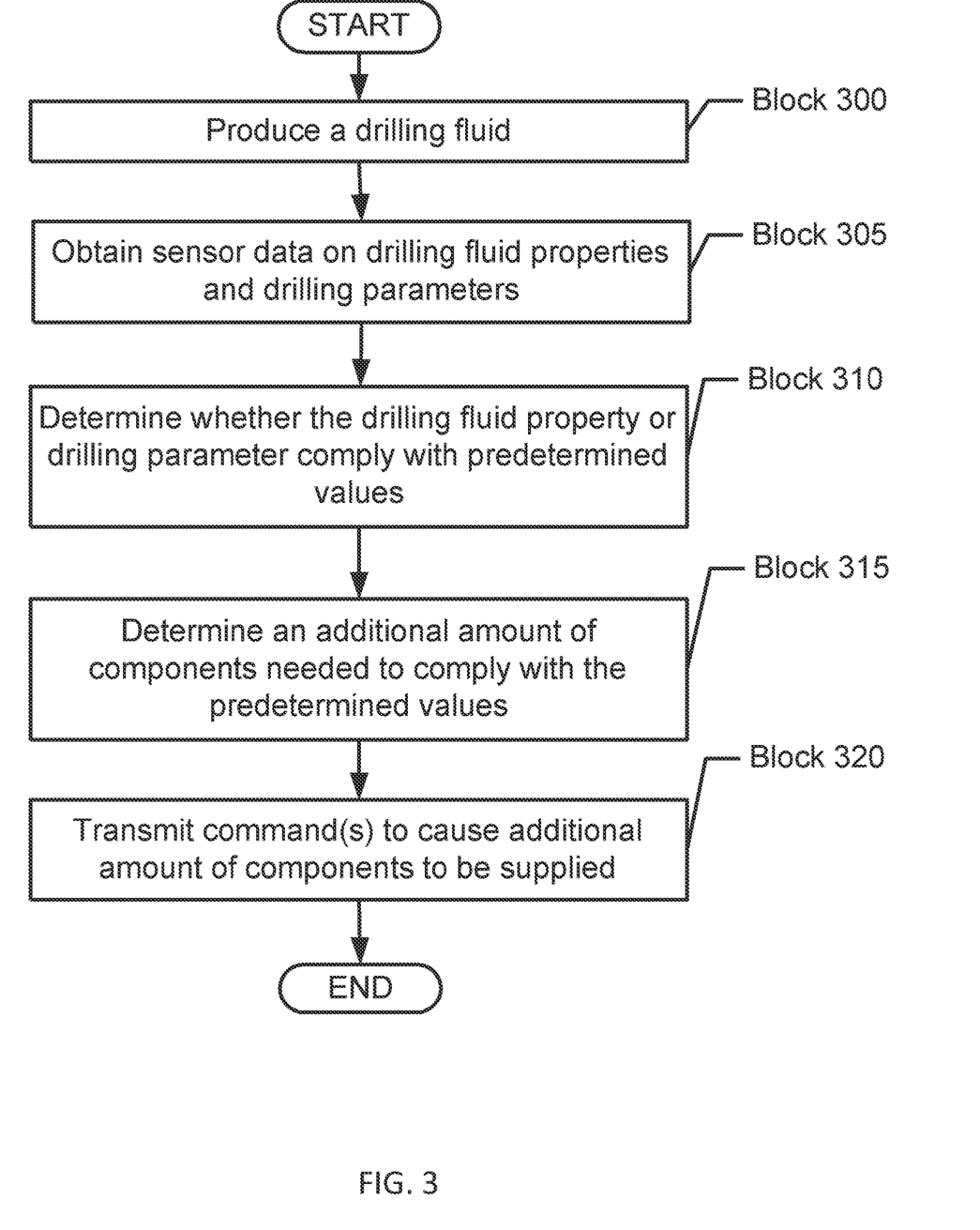
FIG. 3 shows a flowchart of a method for producing a drilling fluid.

FIG. 3 shows a flowchart in accordance with one or more embodiments. Specifically, FIG. 3 describes a specific method for producing a drilling fluid. One or more blocks in FIG. 3 may be performed by one or more components as described in FIGS. 1 and 2. While the various blocks in FIG. 3 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 300, components of a drilling fluid, including various liquids, fresh mud, recycled mud, additives, and/or other chemicals, are supplied to an active pit and mixed to produce a drilling fluid in accordance with one or more embodiments. The amount of each component may be determined based on desired drilling fluid property for a particular wellbore or desired parameters in drilling operation. For example, a drilling fluid may be designed to have preselected drilling fluid properties based on, at least in part, the type of rock being drilled, the orientation of the well (horizontal, vertical, or directional), the expected type of formation fluid, and downhole pressure and temperature conditions. Once produced, the drilling fluid in the active pit may be introduced to the wellbore for circulation in the drilling system.

In Block 305, sensor data with regard to drilling fluid properties and drilling parameters may be obtained from one or more sensors in the drilling system in accordance with one or more embodiments to monitor the drilling fluid in circulation.

According to embodiments of the present disclosure, sensor data may indicate initial drilling fluid properties, before the drilling fluid is directed into the wellbore, such as initial lubricant content and/or initial coefficient of friction. Fluids and structures positioned along a process path prior to entering a well may be referred to as being upstream from the well. In some embodiments, sensor data may indicate used drilling fluid properties, after used drilling fluid is directed out of the well, such as returned lubricant content and/or coefficient of friction. Fluids and structures positioned along a process path after exiting the well may be referred to as being downstream from the well.

For example, one or more upstream sensors may be positioned along an upstream flowline or equipment from which the drilling fluid is directed into a well, e.g., discharge line 134 or active pit 131, to measure initial drilling fluid properties, before the drilling fluid is directed into the wellbore. Upstream flowlines or equipment may be located between the drilling fluid source (e.g., including an active pit) and the drill string.

One or more sensors may also be positioned along a downstream flowline or equipment located between and including a wellbore outlet and return equipment in a drilling fluid processing system, e.g., returning flowline 135 or filter equipments 136a to 136d, to measure used drilling fluid properties, after used drilling fluid is directed out of the well. In some embodiments, downstream sensor(s) may be positioned in a used drilling fluid collection pit to measure used drilling fluid properties, after used drilling fluid is directed out of the well.

According to embodiments of the present disclosure, sensor data may also indicate drilling parameters, such as flow rate, pump pressure, torque, revolution per minute, and weight on bit, etc.

In Block 310, a determination is made on whether a drilling fluid property and/or drilling parameter comply with predetermined values. The determination is based on sensor data obtained from one or more sensors in accordance with one or more embodiments. The predetermined values may be input through a use device of the automated control system, or may be calculated by the automated control system. The predetermined value may be the same as the sensor data of the drilling fluid before being introduced downhole, for example, sensor data from a sensor in the active pit or other upstream equipment. If the determination indicates that the drilling fluid complies with the predetermined values, the process shown in FIG. 3 may proceed back to Block 305. If the determination indicates that the drilling fluid does not comply with the predetermined values, the process shown may proceed to Block 315.

During drilling operations, a decrease in the lubricant content and increase in the coefficient of friction in the drilling fluid may occur as the drilling fluid is circulated downhole. For example, lubricant content may be lost by evaporation, lost in filter equipment such as shakers, or lost on drill cuttings. Accordingly, it is expected that the lubricant content of used drilling fluid may be less than the lubricant content of the initially formed drilling fluid (prior to being pumped downhole). Based on such expectations, predetermined values for drilling fluid properties may be calculated to provide desired functionality to the drilling fluid during use. For example, a predetermined value for lubricant content in an initial drilling fluid may be selected to provide an amount of torque reduction (and coefficient of friction reduction) to the drill string and bit during drilling operations. The predetermined value for the lubricant content in the initial drilling fluid (upstream of the well) may be selected based on, for example, the expected amount of lubricant content reduction, the type of well being drilled (e.g., horizontal or vertical), and the type of drilling fluid (e.g., WBM or OBM).

In some embodiments, the expected amount of lubricant loss (e.g., from evaporation or collection into other well system equipment or cuttings) may be used to determine a predetermined value for used drilling fluid properties (downstream of the well).

In one or more embodiments, predetermined values of coefficient of frication and lubricant content may be determined and input to the automated control system. At least two coefficient of friction sensors measure real-time coefficient of frictions of the drilling fluid at upstream and downstream, respectively. The sensor data at upstream and/or downstream may be compared to the predetermined values for the determination, to evaluate whether additional amount of components needs to be supplied. In one or more embodiments, the sensor data at upstream and downstream may be compared to each other, to evaluate the loss during circulation and to evaluate whether additional amounts of components needs to be supplied. In one or more embodiments, the sensor data at upstream and downstream may be compared to each other and compared to the predetermined value.

By comparing upstream and downstream sensor data to each other and to the predetermined value, a cause of discrepancies between such values may be determined and fixed. For example, in some embodiments, sensor data for a downstream drilling fluid property (e.g., coefficient of friction or lubricant content) may be measured as being less than the predetermined value. The downstream measured value may be compared with an upstream measured value (e.g., coefficient of friction or lubricant content in the upstream drilling fluid) to determine if both upstream and downstream values are lower. This may indicate a problem with the ratio of lubricant to drilling fluid in the initial drilling fluid mix. In such case, the problem may be remedied to provide the correct ratio in subsequent mixing of the drilling fluid. In some embodiments, if the upstream sensor data is lower than the predetermined value, but the downstream sensor data falls within the predetermined value, this may indicate a greater than anticipated loss of lubricant during drilling. In such case, a determination may be made, for example, if there is a defect in the drilling system or drilling parameter that should be changed and/or if the upstream lubricant content should be increased to account for the greater than anticipated loss of lubricant during drilling.

In Block 315, a determination is made to adjust the amount of components to be supplied in producing the drilling fluid. The determination may be made, at least in part, based on whether the drilling fluid is WBM or OBM. Depending on different continuous phases of the drilling fluid, the automated control system may determine what components are needed and an additional amount of drilling fluid components needed, such that the drilling fluid complies with the predetermined values to have desired properties. For example, if the drilling fluid contains WBM and the determination result of Block 310 indicates that a coefficient of friction of the used drilling fluid in the flowline is greater than a predetermined coefficient of friction value, a type of WBM lubricant is determined and an additional amount of lubricant needed is calculated. The calculation may be based on the sensor data with regard to other drilling fluid property and drilling parameters, such as flow rate, total circulating volume, pump pressure, torque, revolution per minute, and weight on bit. The calculation may also be based on the well volume, surface pits volume, etc. An algorithm that is commonly known in the art may be used for the determination.

In some embodiments, the determination step in Block 315 may include using a lubricant concentration value for providing an optimal friction coefficient for a selected type of drilling fluid and a selected application. Such lubricant concentration value may be obtained from a laboratory evaluation prior to drilling the well.

According to embodiments of the present disclosure, a calculation of an amount of lubricant to be added to a drilling fluid to adjust to predetermined values may include the following steps: A computer may be in communication with or have access to the drilling rig parameters data and will get the following well volume and surface pits volume (which can be input manually or through the network). Those two parameters may be used to calculate the total circulating volume. Based on the lubricant content values collected from active pit and flowline sensors, a required lubricant volume addition may be calculated. The difference between the predetermined value minus the flowline sensor value (in percentage by volume) may be multiplied by the total circulating volume to determine the required volume of lubricant to be added to the calculated circulating volume. An example calculation is shown below merely for illustrative purposes:

Example 1

Lubricant content Predetermine value (A): 3% v/v
Flowline sensor value (B): 1% v/v
Pit sensor value (C): 1% v/v
Total Circulating volume (D): 1,000 barrels $$\text{Required Lubricant addition} = (A - B) \times D$$
$$= (3\% - 1\%) \times 1{,}000 \text{ barrels}$$
$$= 2\% \times 1{,}000 \text{ barrels}$$
$$= 20 \text{ barrels}$$

In Example 1, the required lubricant addition to the total circulating system will be 20 barrels of lubricant.

In Block 325, a command is transmitted from the automated control system to cause additional amount of one or more components, for example lubricants, to be supplied to the active pit. According to embodiments of the present disclosure, lubricant additions may be done automatically and gradually until pit and flowline sensors indicate that a predetermined value has been achieved.

Figure 4:
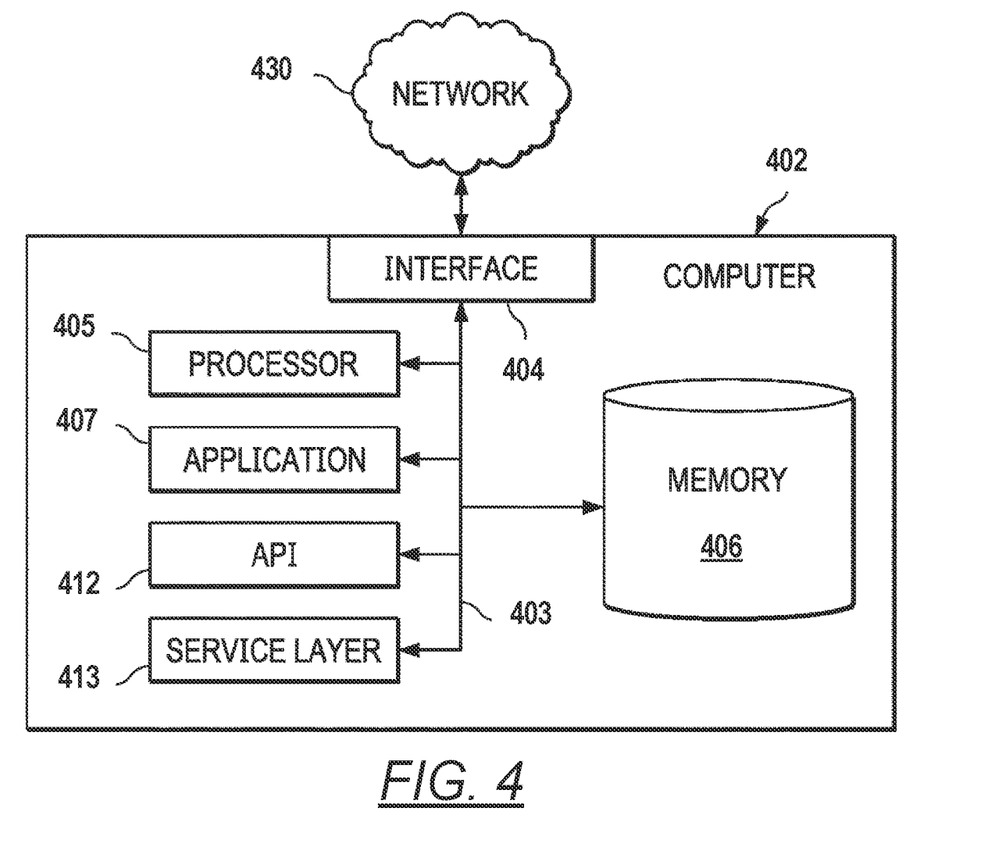
FIG. 4 shows a computer system in accordance with one or more embodiments.

One or more embodiments described herein may be implemented on a computer system. FIG. 4 is a block diagram of a computer system 402 used to provide computational functionalities associated with described algorithms, methods, functions, processes, flows, and procedures as described in the instant disclosure, according to an implementation. The illustrated computer 402 is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer 402 may include a computer that includes an input device, such as a keypad, keyboard, touch screen, or other device that can accept user information, and an output device that conveys information associated with the operation of the computer 402, including digital data, visual, or audio information (or a combination of information), or a GUI.

The computer 402 can serve in a role as a client, network component, a server, a database or other persistency, or any other component (or a combination of roles) of a computer system for performing the subject matter described in the instant disclosure. The illustrated computer 402 is communicably coupled with a network 430. In some implementations, one or more components of the computer 402 may be configured to operate within environments, including cloud-computing-based, local, global, or other environment (or a combination of environments).

At a high level, the computer 402 is an electronic computing device operable to receive, transmit, process, store, or manage data and information associated with the described subject matter. According to some implementations, the computer 402 may also include or be communicably coupled with an application server, e-mail server, web server, caching server, streaming data server, business intelligence (BI) server, or other server (or a combination of servers).

The computer 402 can receive requests over network 430 from a client application (for example, executing on another computer 402) and responding to the received requests by processing the said requests in an appropriate software application. In addition, requests may also be sent to the computer 402 from internal users (for example, from a command console or by other appropriate access method), external or third-parties, other automated applications, as well as any other appropriate entities, individuals, systems, or computers.

Each of the components of the computer 402 can communicate using a system bus 403. In some implementations, any or all of the components of the computer 402, both hardware or software (or a combination of hardware and software), may interface with each other or the interface 404 (or a combination of both) over the system bus 403 using an application programming interface (API) 412 or a service layer 413 (or a combination of the API 412 and service layer 413. The API 412 may include specifications for routines, data structures, and object classes. The API 412 may be either computer-language independent or dependent and refer to a complete interface, a single function, or even a set of APIs. The service layer 413 provides software services to the computer 402 or other components (whether or not illustrated) that are communicably coupled to the computer 402. The functionality of the computer 402 may be accessible for all service consumers using this service layer. Software services, such as those provided by the service layer 413, provide reusable, defined business functionalities through a defined interface. For example, the interface may be software written in JAVA, C++, or other suitable language providing data in extensible markup language (XML) format or other suitable format. While illustrated as an integrated component of the computer 402, alternative implementations may illustrate the API 412 or the service layer 413 as stand-alone components in relation to other components of the computer 402 or other components (whether or not illustrated) that are communicably coupled to the computer 402. Moreover, any or all parts of the API 412 or the service layer 413 may be implemented as child or sub-modules of another software module, enterprise application, or hardware module without departing from the scope of this disclosure.

The computer 402 includes an interface 404. Although illustrated as a single interface 404 in FIG. 4, two or more interfaces 404 may be used according to particular needs, desires, or particular implementations of the computer 402. The interface 404 is used by the computer 402 for communicating with other systems in a distributed environment that are connected to the network 430. Generally, the interface 404 includes logic encoded in software or hardware (or a combination of software and hardware) and operable to communicate with the network 430. More specifically, the interface 404 may include software supporting one or more communication protocols associated with communications such that the network 430 or interface's hardware is operable to communicate physical signals within and outside of the illustrated computer 402.

The computer 402 includes at least one computer processor 405. Although illustrated as a single computer processor 405 in FIG. 4, two or more processors may be used according to particular needs, desires, or particular implementations of the computer 402. Generally, the computer processor 405 executes instructions and manipulates data to perform the operations of the computer 402 and any algorithms, methods, functions, processes, flows, and procedures as described in the instant disclosure.

The computer 402 also includes a memory 406 that holds data for the computer 402 or other components (or a combination of both) that can be connected to the network 430. For example, memory 406 can be a database storing data consistent with this disclosure. Although illustrated as a single memory 406 in FIG. 4, two or more memories may be used according to particular needs, desires, or particular implementations of the computer 402 and the described functionality. While memory 406 is illustrated as an integral component of the computer 402, in alternative implementations, memory 406 can be external to the computer 402.

The application 407 is an algorithmic software engine providing functionality according to particular needs, desires, or particular implementations of the computer 402, particularly with respect to functionality described in this disclosure. For example, application 407 can serve as one or more components, modules, applications, etc. Further, although illustrated as a single application 407, the application 407 may be implemented as multiple applications 407 on the computer 402. In addition, although illustrated as integral to the computer 402, in alternative implementations, the application 407 can be external to the computer 402.

There may be any number of computers 402 associated with, or external to, a computer system containing computer 402, each computer 402 communicating over network 430. Further, the term "client," "user," and other appropriate terminology may be used interchangeably as appropriate without departing from the scope of this disclosure. Moreover, this disclosure contemplates that many users may use one computer 402, or that one user may use multiple computers 402.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A method, comprising:
   mixing, in an active pit, a drilling fluid to be introduced to a wellbore;
   receiving, through a flowline, the drilling fluid from the wellbore;
   obtaining sensor data, using sensors disposed in the active pit and in the flowline, on coefficient of friction and lubricant content of the drilling fluid before and after being introduced to the wellbore; and
   comparing a first piece of the sensor data obtained at the active pit, a second piece of the sensor data obtained at the flowline, and predetermined values of coefficient of friction and lubricant content, for evaluating a loss of the drilling fluid and for determining whether a lubricant needs to be added to the drilling fluid.

2. The method of claim 1, further comprising obtaining, by a user device, the predetermined value.

3. The method of claim 1, further comprising calculating an additional amount of lubricant needed to comply with the predetermined value.

4. The method of claim 3, wherein the calculating is based on a volume of the drilling fluid in circulation and a difference between the sensor data and the predetermined value.

5. The method of claim 3, further comprising transmitting a command to cause the additional amount of lubricant to be supplied to the drilling fluid.

6. The method of claim 1, further comprising selecting a type of lubricant based on whether the drilling fluid contains water-based mud or oil-based mud.

7. A system, comprising:
   an active pit containing a drilling fluid to be introduced to a wellbore;
   a flowline receiving the drilling fluid from the wellbore, sensors disposed in the active pit and in the flowline and configured to obtain sensor data on at least one of coefficient of friction and lubricant content of the drilling fluid before and after being introduced to the wellbore; and
   an automated control system configured to make a determination on whether a lubricant needs to be added to the drilling fluid and configured to evaluate a loss of the drilling fluid, by comparing a first piece of the sensor data obtained at the active pit, a second piece of the sensor data obtained at the flowline, and predetermined values of coefficient of friction and lubricant content.

8. The system of claim 7, further comprises a user device for inputting the predetermined value.

9. The system of claim 7, wherein the automated control system is configured to calculate an additional amount of lubricant needed to comply with the predetermined value.

10. The system of claim 9, wherein the automated control system is configured to calculate the additional amount based on a volume of the drilling fluid in circulation and a difference between the sensor data and the predetermined value.

11. The system of claim 9, wherein the automated control system is configured to transmit a command to cause the additional amount of lubricant to be supplied to the drilling fluid.

12. The system of claim 7, wherein the automated control system is configured to select a type of lubricant based on whether the drilling fluid contains water-based mud or oil-based mud.

* * * * *